United States Patent
Kuwabara et al.

(10) Patent No.: US 9,462,990 B2
(45) Date of Patent: Oct. 11, 2016

(54) RADIATION IMAGING SYSTEM AND CONTROL METHOD THEREOF, AND RADIATION IMAGE DETECTING DEVICE

(71) Applicant: FUJIFILM Corporation, Tokyo (JP)

(72) Inventors: Takeshi Kuwabara, Ashigarakami-gun (JP); Takeshi Kamiya, Ashigarakami-gun (JP); Yusuke Kitagawa, Ashigarakami-gun (JP); Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 433 days.

(21) Appl. No.: 14/228,537

(22) Filed: Mar. 28, 2014

(65) Prior Publication Data

US 2014/0211922 A1 Jul. 31, 2014

Related U.S. Application Data

(63) Continuation of application No. PCT/JP2012/074500, filed on Sep. 25, 2012.

(30) Foreign Application Priority Data

Sep. 29, 2011 (JP) .................................. 2011-214199

(51) Int. Cl.
G03B 42/02 (2006.01)
A61B 6/00 (2006.01)

(52) U.S. Cl.
CPC ................. *A61B 6/542* (2013.01); *A61B 6/54* (2013.01); *A61B 6/56* (2013.01); *A61B 6/4233* (2013.01); *A61B 6/4283* (2013.01); *A61B 6/585* (2013.01); *G03B 42/02* (2013.01)

(58) Field of Classification Search
CPC .... A61B 6/4233; A61B 6/4283; A61B 6/54; A61B 6/542; A61B 6/56; A61B 6/585; G03B 42/02
See application file for complete search history.

(56) References Cited

U.S. PATENT DOCUMENTS 7,078,701 B2 7/2006 Ishii et al.
7,856,085 B2 12/2010 Hayashida
(Continued)

FOREIGN PATENT DOCUMENTS

JP 2005-198801 A 7/2005
JP 2006-116205 A 5/2006
(Continued)

OTHER PUBLICATIONS

Machine translation of JP2006116205A1.*
(Continued)

*Primary Examiner* — David J Makiya
*Assistant Examiner* — John Corbett
(74) *Attorney, Agent, or Firm* — Birch, Stewart, Kolasch & Birch, LLP

(57) ABSTRACT

Upon input of a synchronization signal, which indicates a start of an X-ray emission, from a source control unit for controlling an X-ray source, an electronic cassette makes an FPD start an accumulation operation and measurement of an X-ray dose. The electronic cassette and a console command their communicators to stop communication of any signal other than a stop signal, which stops the X-ray emission from the X-ray source, during the accumulation operation of the FPD. As soon as the X-ray dose has reached a predetermined threshold value, the electronic cassette transmits the stop signal to the source control unit through the console. A delay in transmission of the stop signal due to communication congestion or signal collision does not occur, because the electronic cassette and the console stop the communication of the signal other than the stop signal.

29 Claims, 7 Drawing Sheets

(56) References Cited

U.S. PATENT DOCUMENTS

| | | | |
|---|---|---|---|
| 2008/0319312 A1* | 12/2008 | Eichler | A61B 5/06 600/424 |
| 2009/0220048 A1 | 9/2009 | Ohta et al. | |
| 2010/0034356 A1 | 2/2010 | Hayashida | |
| 2010/0187427 A1* | 7/2010 | Kuwabara | A61B 6/56 250/370.08 |
| 2010/0320392 A1 | 12/2010 | Nishino et al. | |

FOREIGN PATENT DOCUMENTS

| | | |
|---|---|---|
| JP | 2009-201874 A | 9/2009 |
| JP | 2010-35778 A | 2/2010 |
| JP | 2010-57525 A | 3/2010 |
| WO | WO 01/76228 A1 | 10/2001 |
| WO | WO 2006/101234 A1 | 9/2006 |

OTHER PUBLICATIONS

Extended European Search Report, dated Mar. 31, 2015, for European Application No. 12835269.7.

The Intl. Preliminary Report on Patentability and Written Opinion of the Intl Searching Authority w/ English language translation thereof (Forms PCT/IB/326, PCT/IB/373, PCT/ISA/237 and PCT/IB/373), dated Apr. 10, 2014 for Intl. Appl. No. PCT/JP2012/074500.

* cited by examiner

RADIATION IMAGING SYSTEM AND CONTROL METHOD THEREOF, AND RADIATION IMAGE DETECTING DEVICE

BACKGROUND OF THE INVENTION

1. Field of the Invention

The present invention relates to a radiation imaging system for imaging a radiographic image of an object and a control method thereof, and a radiation image detecting device used in the radiation imaging system.

2. Description Related to the Prior Art

In a medical field, an X-ray imaging system using X-rays, for example as a kind of radiation, is known. The X-ray imaging system is constituted of an X-ray generating apparatus for applying the X-rays to an object and an X-ray image detecting device, which receives the X-rays passed through the object and detects an X-ray image representing image information of the object. In the X-ray image detecting device, an X-ray film, an imaging plate (IP), or the like is conventionally used as a detection panel. However, an X-ray image detecting device using a flat panel detector (FPD) as the detection panel has become widespread presently. The FPD has a matrix of pixels each for accumulating signal charge in accordance with the amount of the X-rays incident thereon. The FPD converts the accumulated signal charge into a voltage signal on a pixel-by-pixel basis at its signal processing circuit, and thereby detects the X-ray image representing the image information of the object and outputs the X-ray image as digital image data.

Some X-ray imaging systems have an automatic exposure control (AEC) function in which a photo timer disposed in front of an X-ray imaging apparatus measures a dose of the X-rays passed through the object and issues a stop signal to the X-ray generating apparatus to stop an X-ray emission, as soon as the X-ray dose has reached a predetermined value. There is also known an X-ray image detecting device that carries out the AEC using a part of pixels of the FPD or a dose detection sensor disposed in an image capturing field of the FPD, instead of the photo timer (for example, refer to U.S. Pat. No. 7,078,701 corresponding to Japanese Patent Laid-Open Publication No. 2004-251892). In performing the AEC in the X-ray image detecting device having the integral dose detection sensor, the X-ray image detecting device issues the stop signal to the X-ray generating apparatus. The photo timer itself is an X-ray absorber that absorbs the X-rays of the order of approximately 5%. Thus, using the photo timer in the AEC requires an X-ray dose to be increased by an X-ray absorption amount by the photo timer, and hence causes increase in radiation exposure of the object. Using the X-ray sensor of the FPD, contrarily, does not bring about such a problem.

In the X-ray imaging system using the X-ray image detecting device having the FPD, communication of various types of signals and data is established among the X-ray generating apparatus, the X-ray image detecting device, and a console. The console is a device for setting an imaging condition and displaying the captured X-ray image. The console transmits to the X-ray image detecting device a life check signal for checking whether or not the X-ray image detecting device is activated, a state monitoring signal for making an inquiry about a state such as a temperature to the X-ray image detecting device, a calibration command for commanding the X-ray image detecting device to perform a calibration, and the like. The X-ray image detecting device transmits to the console a response signal responding to each of the above signals, an error signal for making a notification of an error, captured X-ray image data, and the like. The X-ray generating apparatus and the X-ray image detecting device transmit and receive therebetween a synchronization signal for notifying the X-ray image detecting device of a start of an X-ray emission from the X-ray generating apparatus, the stop signal for making the X-ray generating apparatus stop the X-ray emission, a response signal for making a notification of the stop of X-ray emission, and the like.

As described above, the X-ray image detecting device communicates the various types of signals with the console. Furthermore, the synchronization signal is communicated before the start of an X-ray emission between the X-ray image detecting device and the X-ray generating apparatus, in order to synchronize X-ray emission timing by the X-ray generating apparatus and image accumulation timing by the X-ray image detecting device. Additionally, in performing the AEC, the stop signal is communicated between the X-ray image detecting device and the X-ray generating apparatus.

In the communication among the essential devices of the X-ray imaging system, e.g. between the X-ray image detecting device and the console and between the X-ray image detecting device and the X-ray generating apparatus, communications line congestion and signal collision cause the occurrence of a communication delay. The communications line congestion means a case where a plurality of signals heading for the same direction are transmitted at almost the same time through a communications line. The signal collision means a collision of signals transmitted in both directions of the communications line.

As measures against the communication delay in the synchronization signal between the X-ray image detecting device and the X-ray generating apparatus, according to an X-ray imaging system of U.S. Pat. No. 7,856,085 corresponding to Japanese Patent Laid-Open Publication No. 2010-035778, for example, it is judged that whether a communications method between the devices adopts dedicated line communications, wireless communications, or network communications. In the case of the wireless communications or the network communications in which the communication delay tends to occur, FPD drive timing is changed in anticipation of the communication delay.

To be more specific, according to the X-ray imaging system of the U.S. Pat. No. 7,856,085, the X-ray image detecting device issues a preparation completion signal to the X-ray generating apparatus, when being ready for receiving an X-ray emission. Upon receiving the preparation completion signal, the X-ray generating apparatus starts an X-ray emission. An emission time of the X-rays is set in advance, and the X-ray generating apparatus stops the X-ray emission after a lapse of the emission time. In the X-ray image detecting device, the issue of the preparation completion signal triggers a start of an image accumulation operation. An image accumulation time is set longer than the emission time such that the image accumulation operation has been continued during the set emission time. In a case where the communications method is the wireless communications or the network communications excepting the dedicated line communications, the communication of the preparation completion signal is delayed more than that in the case of the dedicated line communications, and thereby the timing of starting the X-ray emission is delayed. The larger the communication delay, the more the timing of starting the X-ray emission is delayed. At the worst, such a situation may occur that the X-ray generating apparatus keeps emitting the X-rays even after the X-ray image detecting device completes the image accumulation operation. To handle such a problem, in the X-ray imaging system of the U.S. Pat. No. 7,856,085, the FPD drive timing is varied in the communications method without using the dedicated line to make the image accumulation time longer than that of the dedicated line communications.

Also, as measures against a communication delay between the X-ray image detecting device and the console, according to an X-ray imaging system of Japanese Patent Laid-Open Publication No. 2010-057525, for example, bidirectional communications between the X-ray image detecting device and the console is withdrawn in order to prevent a delay in communication of imaging order information due to the signal collision, and using unidirectional communications prevents the communication delay.

As described above, the U.S. Pat. No. 7,856,085 describes the measures against the communication delay in the synchronization signal (preparation completion signal) at a time of starting communication between the X-ray image detecting device and the X-ray generating apparatus. The Japanese Patent Laid-Open Publication No. 2010-057525 describes the measures against the communication delay between the X-ray image detecting device and the console.

In carrying out the AEC, as described in the X-ray imaging system of the U.S. Pat. No. 7,078,701, it is required that the stop signal is transmitted without a delay from the X-ray image detecting device to the X-ray generating apparatus. This is because a delay occurring in the stop signal prevents the X-ray emission from stopping at an appropriate time, and therefore brings about increase in the radiation exposure of the object. The delay in stopping the X-ray emission also causes application of the X-rays beyond a target dose, and hence results in deterioration in the quality of the X-ray image.

The methods described in the U.S. Pat. No. 7,856,085 and the Japanese Patent Laid-Open Publication No. 2010-057525 have no consideration for the AEC, and adopting these methods does not become measures directed toward the elimination of the communication delay in the stop signal. The method of the U.S. Pat. No. 7,856,085 relates to measures against a delay in emission start timing due to a delay in synchronization communication at a time of starting the emission. Elongating the image accumulation time in anticipation of the communication delay cannot solve the communication delay in the stop signal, as a matter of course.

In the method of the Japanese Patent Laid-Open Publication No. 2010-057525, the communication method between the console and the X-ray image detecting device is limited to the unidirectional communications from the console to the X-ray image detecting device, for the purpose of preventing the communication delay in transmitting the order information from the console to the X-ray image detecting device. In performing the AEC, the console sometimes mediates the transmission of the stop signal from the X-ray image detecting device to the X-ray generating apparatus. In such a case, the stop signal has to be transmitted from the X-ray image detecting device to the console. Furthermore, the bidirectional communications of the various types of signals is required between the X-ray image detecting device and the console, which includes a transmission of the life check signal for checking an actuation state of the X-ray image detecting device and a response thereof, a transmission of the state monitoring signal for monitoring the state such as the temperature of the X-ray image detecting device and a response thereof, and the like, in addition to a transmission and a response of the order information and the stop signal. Thus, adopting this unidirectional communications is unrealistic.

SUMMARY OF THE INVENTION

The present invention aims at providing a radiation imaging system and a control method thereof, and a radiation image detecting device that can prevent a delay in communication of the stop signal for stopping an X-ray emission. To achieve the above and other objects of the present invention, a radiation imaging system according to the present invention includes a radiation image detecting device and a console for controlling the radiation image detecting device. The radiation image detecting device includes an image detector, a dosimeter, a stop signal issuing unit, a first communicator, and a first controller. The image detector has an image capturing field having an array of a plurality of pixels for accumulating an electric signal in accordance with an incident amount of radiation from a radiation generating apparatus, and detects a radiographic image. The dosimeter measures a dose of the radiation emitted from the radiation generating apparatus and passed through an object. The stop signal issuing unit issues a stop signal to make the radiation generating apparatus stop an emission of the radiation in accordance with the dose of the radiation measured by the dosimeter. The first communicator performs communication processing of the stop signal for transmitting the stop signal to the radiation generating apparatus during an accumulation operation of the image detector, and performs communication processing of a signal other than the stop signal. The first controller controls the first communicator. The console includes a second communicator and a second controller. The second communicator performs communication processing of a control signal for transmitting the control signal to the first communicator. The second controller controls the second communicator. During the accumulation operation, communication regulation for regulating communication of a signal other than the stop signal between the first communicator and the second communicator is performed by controlling at least one of the first controller and the second controller, at least until the first communicator completes transmission of the stop signal.

The signal to which the communication regulation is applied preferably includes the control signal. The control signal includes at least one of a life check signal for checking an actuation state of the radiation image detecting device, a state monitoring signal for checking a state including a temperature of the radiation image detecting device, and a calibration command for commanding the radiation image detecting device to execute a calibration. The stop signal is transmitted to the radiation generating apparatus through the console, for example.

The communication regulation preferably includes processing in which at least one of the first communicator and the second communicator stops all or a part of communication of the signals other than the stop signal. The second controller of the console stops transmitting the control signal from the second communicator to the first communicator to carry out the communication regulation. The first controller of the radiation image detecting device stops communication of the signal other than the stop signal from the first communicator to carry out the communication regulation.

The communication regulation carried out by at least one of the first controller and the second controller is lifted after the first communicator completes transmission of the stop signal. Otherwise, the communication regulation is preferably lifted after receiving a response signal for indicating a stop of the emission of the radiation from the radiation source, after completing the accumulation operation and furthermore completing a readout operation for reading out the radiographic image from the image detector, or after the dosimeter has detected an actual stop of the emission of the radiation.

The radiation image detecting device has one the first communicator that is shared between communication of the stop signal and communication of the signal other than the stop signal. Only one communication port is connected to the first communicator, and the communication port is shared between communication of the stop signal and communication of the signal other than the stop signal. Otherwise, a plurality of communication ports may be connected to the first communicator, and one of the communication ports may be dedicated to transmission of the stop signal.

In the radiation image detecting device, a dose detection sensor is preferably provided in the image capturing field of the image detector to output a dose detection signal to the dosimeter. The dose detection sensor preferably uses a part of the pixels.

The radiation image detecting device is preferably an electronic cassette having the image detector contained in a portable housing.

A control method of a radiation imaging system, having a radiation image detecting device and a console for controlling the radiation image detecting device, includes the steps of accumulating an electric signal in a plurality of pixels arranged in an image capturing field in accordance with an incident amount of radiation from a radiation generating apparatus to detect a radiographic image in the radiation image detecting device; measuring a dose of the radiation emitted from the radiation generating apparatus and passed through an object in the radiation image detecting device; issuing a stop signal to be transmitted to the radiation generating apparatus to make the radiation generating apparatus stop an emission of the radiation in accordance with the measured dose, in the radiation image detecting device; and regulating communication of a signal other than the stop signal between the radiation image detecting device and the console in the accumulation step, at least until the radiation image detecting device completes transmission of the stop signal.

A radiation image detecting device according to the present invention includes an image detector, a dosimeter, a stop signal issuing unit, a communicator, and a controller. The image detector has an image capturing field having an array of a plurality of pixels for accumulating an electric signal in accordance with an incident amount of radiation from a radiation generating apparatus, and detects a radiographic image. The dosimeter measures a dose of the radiation emitted from the radiation generating apparatus and passed through an object. The stop signal issuing unit issues a stop signal to make the radiation generating apparatus stop an emission of the radiation in accordance with the dose of the radiation measured by the dosimeter. The communicator performs communication processing of the stop signal for transmitting the stop signal to the radiation generating apparatus during an accumulation operation of the image detector, and performs communication processing of a signal other than the stop signal. The controller regulates communication of the signal other than the stop signal by the communicator during the accumulation operation, at least until the communicator completes transmission of the stop signal.

In the radiation imaging system, the stop signal issuing unit preferably issues the stop signal, upon the dose of the radiation measured by the dosimeter reaching a target dose.

According to the present invention, the communication of the signals other than the stop signal is regulated, while the image detector performs the accumulation operation, at least until transmission of the stop signal is completed. Thus, it is possible to provide a radiation imaging system and a control method thereof, and a radiation image detecting device that can prevent a delay of the stop signal. Accordingly, it is possible to stop the emission of the radiation from the radiation source at appropriate timing, and hence reduce unnecessary radiation exposure of the object. Furthermore, stopping the emission at appropriate timing prevents application of an excessive dose beyond a target dose, and results in preventing degradation in the quality of the radiographic image.

BRIEF DESCRIPTION OF DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS

Figure 1:
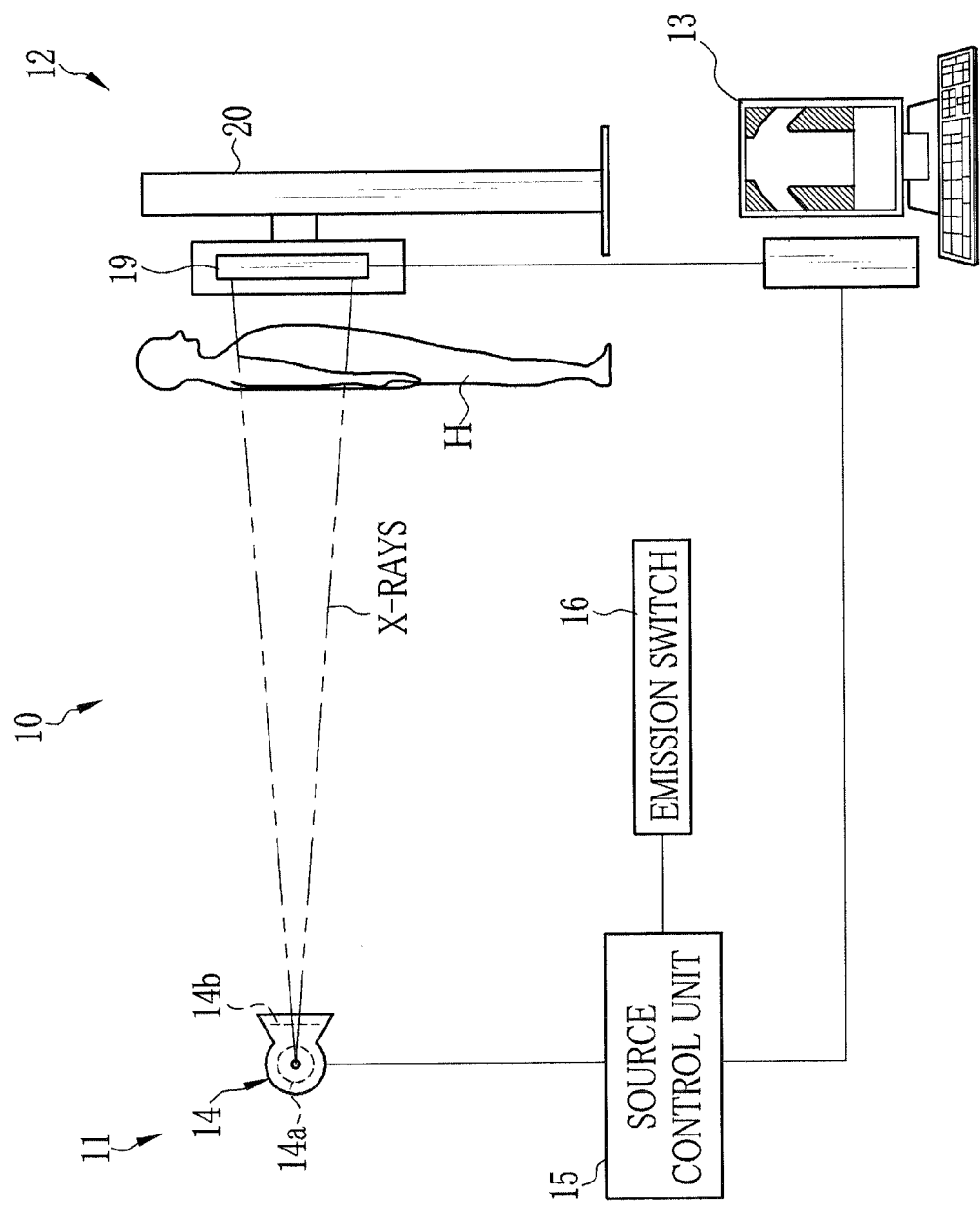
FIG. 1 is an explanatory view showing the schematic structure of an X-ray imaging system.

In FIG. 1, an X-ray imaging system 10 is constituted of an X-ray generating apparatus 11, an X-ray imaging apparatus 12, and a console 13. The X-ray generating apparatus 11 includes an X-ray source 14, a source control unit 15 for controlling the X-ray source 14, and an emission switch 16. The X-ray source 14 has an X-ray tube 14a for radiating X-rays and an irradiation field limiter (collimator) 14b for limiting an irradiation field of the X-rays radiating from the X-ray tube 14a.

The X-ray tube 14a has a cathode composed of a filament for emitting thermoelectrons, and an anode (target) that radiates the X-rays by collision of the thermoelectrons emitted from the cathode. The irradiation field limiter is composed of, for example, four lead plates for blocking the X-rays. The four lead plates are disposed in each side of a rectangle so as to form a rectangular irradiation opening in a middle to pass the X-rays therethrough. Shifting the position of the lead plates varies the size of the irradiation opening to limit the irradiation field.

The source control unit 15 is provided with a high voltage generator, a controller, and a cable-type communicator. The high voltage generator supplies the X-ray source 14 with a high tube voltage. The controller controls the tube voltage for determining the radiation quality (energy spectrum) of the X-rays emitted from the X-ray source 14, a tube current for determining an emission amount per unit of time, and an emission time of the X-rays. The cable-type communicator communicates with the console 13. The high voltage generator generates the high tube voltage by multiplying an input voltage by a transformer, and supplies drive power to the X-ray source 14 through a high voltage cable. An imaging condition including the tube voltage, the tube current, and the emission time is manually set by an operator such as a radiological technician through an operation panel of the source control unit 15. Note that, the imaging condition of the source control unit 15 may be set in the console 13.

The emission switch 16, which is to be operated by the radiological technician, is connected to the source control unit 15 through a signal cable. The emission switch 16 is a two-step press switch. Upon a first-step press of the emission switch 16, a warm-up start signal is issued to start warming up the X-ray source 14. Upon a second-step press, an emission start signal is issued to make the X-ray source 14 start emitting the X-rays. These signals are inputted to the source control unit 15 through the signal cable.

Upon inputting the warm-up start signal from the emission switch 16, the source control unit 15 starts warming up the X-ray source 14 and also communicates a synchronization signal to the X-ray imaging apparatus 12 to synchronize emission start timing of the X-rays. To be more specific, the source control unit 15 transmits to the X-ray imaging apparatus 12 an emission start request signal that asks for permission to start an X-ray emission, and receives an emission permission signal, being a response signal of the emission start request signal, from the X-ray imaging apparatus 12.

Upon receiving the emission permission signal from the X-ray imaging apparatus 12 and the emission start signal from the emission switch 16, the source control unit 15 issues a start command to the X-ray source 14 and starts supplying electric power to the X-ray source 14. Thus, the X-ray source 14 starts an X-ray emission. Concurrently with starting the electric power supply to the X-ray source 14, the source control unit 15 transmits the synchronization signal indicating the start of the X-ray emission to the X-ray imaging apparatus 12, and furthermore actuates an internal timer to start measuring an X-ray emission time.

The X-ray imaging system 10 can carry out AEC in radiography. In performing the AEC, the X-ray imaging apparatus 12 transmits a stop signal to the source control unit 15. Upon receiving the stop signal from the X-ray imaging apparatus 12, the source control unit 15 issues a stop command to the X-ray source 14 and stops the electric power supply to the X-ray source 14. The X-ray source 14 stops the X-ray emission upon receiving the stop command.

The X-ray imaging system 10 can carry out radiography based on the emission time set in the imaging condition, without using the AEC. In this case, the emission time is set in the source control unit 15. The source control unit 15 monitors a lapse of emission time using the timer, and stops the X-ray emission at the instant when the set emission time has elapsed. Note that, even in the case of performing the AEC in radiography, the source control unit 15 monitors a lapse of emission time using the timer. The source control unit 15 stops the X-ray emission at the instant of exceeding a maximum emission time adhering to safety restrictions, even if no stop signal has been received.

Figure 2:
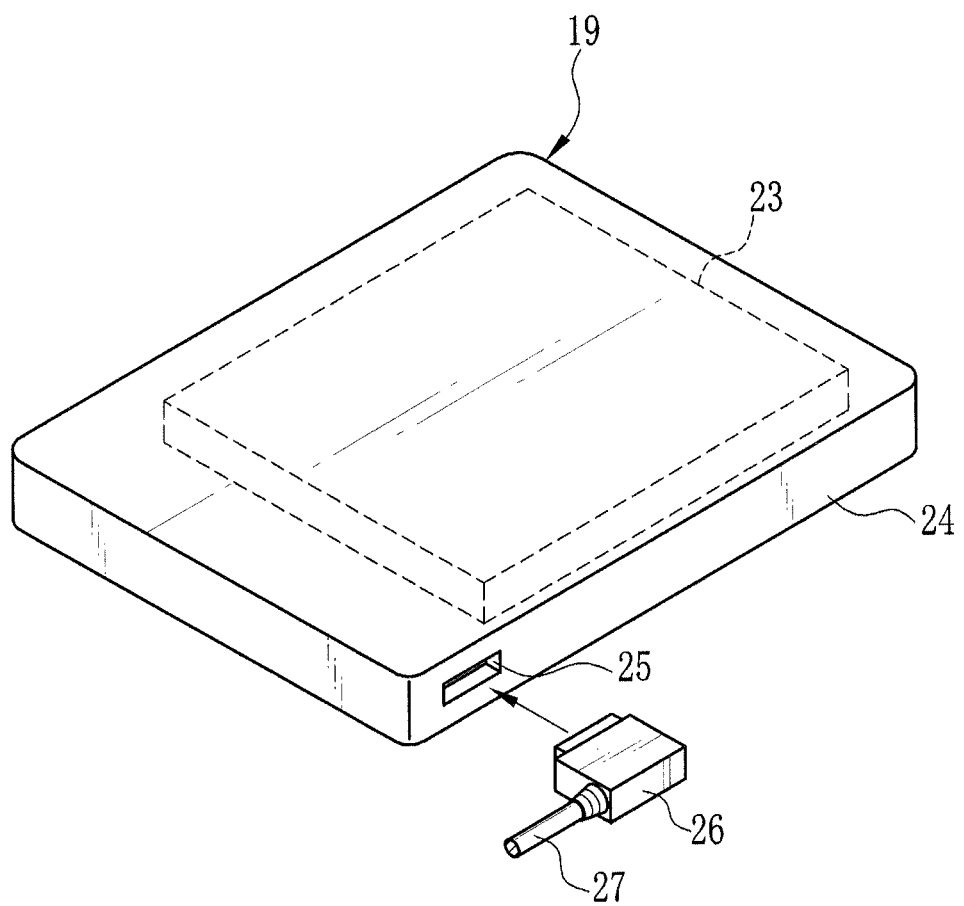
FIG. 2 is an external perspective view showing the structure of an electronic cassette.

The X-ray imaging apparatus 12 is constituted of an electronic cassette 19, which corresponds to a radiation image detecting device of the present invention, and an imaging stand 20. As shown in FIG. 2, the electronic cassette 19 includes an FPD 23 and a portable housing 24 for containing the FPD 23. The electronic cassette 19 receives the X-rays that are emitted from the X-ray source 14 and passed through an object H, and detects an X-ray image of the object H. The housing 24 of the electronic cassette is in an approximately rectangular and flat shape, and of approximately the same size in plane as the size of a film cassette and an IP cassette.

The housing 24 has a multi-terminal 25 at its side surface, into which a communication terminal (communication port) and a power supply terminal are integrated. A multi-connector 26 into which a communication connector and a power supply connector are integrated is fitted into the multi-terminal 25. A multi-cable 27 into which a communication cable and a power supply cable are integrated is connected to the multi-connector 26 at one end. The other end of the multi-cable 27 is provided with a communication connector to be connected to a communication port of the console 13 and a power supply connector to be connected to a power supply for the electronic cassette 19. Thus, the electronic cassette 19 communicates with the console 13 through connection, while being supplied with power from the outside.

The imaging stand 20 has a slot into which the electronic cassette 19 is detachably loaded. The imaging stand 20 holds the electronic cassette 19 in such a position that an incident surface on which the X-rays are incident is opposed to the X-ray source 14. Since the housing of the electronic cassette 19 is of approximately the same size as the size of the film cassette and the IP cassette, the electronic cassette 19 is loadable in an imaging stand designed for the film cassette and the IP cassette. Note that, an upright imaging stand for imaging the object H in a standing position is illustrated as the imaging stand 20, but an imaging bed for imaging the object H in a lying position may be used instead.

Figure 3:
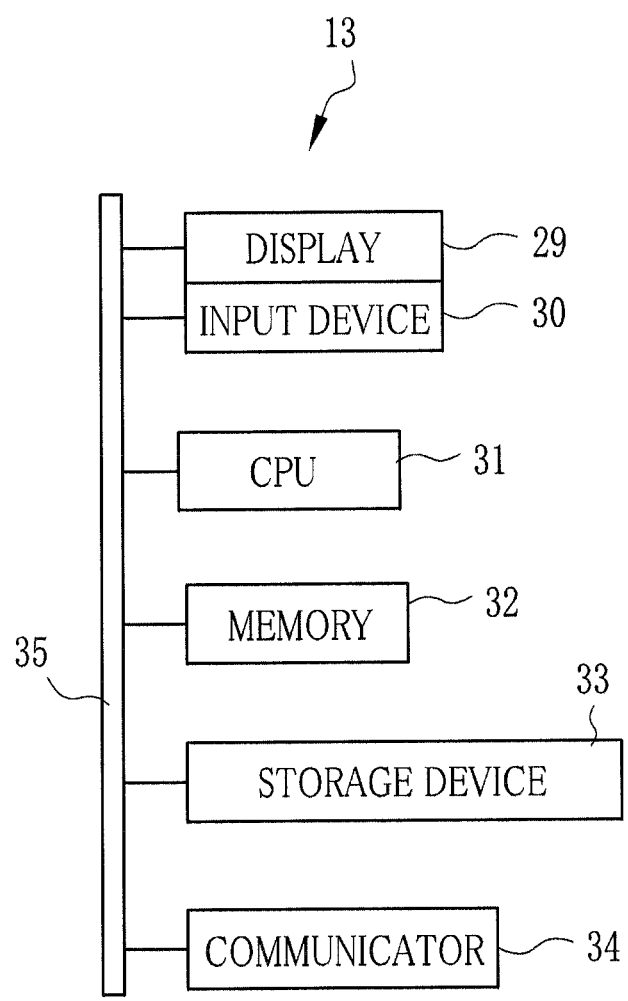
FIG. 3 is a block diagram showing the electrical structure of a console.

As shown in FIG. 3, the console 13 is composed of a display 29 for displaying an imaging order, the X-ray image, and the like, an input device 30 used for inputting the imaging condition and the like, a CPU 31 for controlling the entire console 13, a memory 32 used in a processing operation of the CPU 31, a storage device 33 for storing image data of the X-ray image, and a cable-type communicator 34 communicatably connected to the source control unit 15 and the electronic cassette 19. These parts are connected through a data bus 35.

The console 13 controls the electronic cassette 19 by appropriately communicating a control signal through the communicator 34 with the electronic cassette 19. More specifically, the console 13 periodically transmits to the electronic cassette 19 the control signal, which includes a life check signal for checking whether or not the electronic cassette 19 is activated, a state monitoring signal for making an inquiry about a state such as a temperature of the electronic cassette 19, and the like. The electronic cassette 19 transmits a response signal to the console 13 in response to the control signal transmitted from the console 13. The console 13 executes control in accordance with the contents of the response signal. Furthermore, the control signal to be transmitted from the console 13 to the electronic cassette 19 also includes a calibration command. The console 13 transmits the calibration command to the electronic cassette 19 in predetermined timing, to make the electronic cassette 19 perform a calibration.

Contrarily to the above control signal, an error notification is another control signal to be transmitted from the electronic cassette 19 to the console 13. The error notification is transmitted to the console 13 in case of an error arising in the electronic cassette 19. Upon receiving the error notification from the electronic cassette 19, the console 13 executes control depending on the substance of the error. As described above, out of the control signal to be communicated between the electronic cassette 19 and the console 13, the control signal to be transmitted from the console 13 to the electronic cassette 19 includes the life check signal, the state monitoring signal, the calibration command, and the like, and the control signal to be transmitted from the electronic cassette 19 to the console 13 includes the error notification. The CPU 31 corresponds to a second controller described in claims, and the communicator 34 corresponds to a second communicator of the claims.

The console 13 transmits the imaging condition to the electronic cassette 19 to set up a signal processing condition of the FPD 23. The console 13 also performs synchronization control to synchronize the start and stop timing of an X-ray emission by the X-ray generating apparatus 11 and accumulation and readout operations of the FPD 23, by mediating the transmission and reception of the synchronization signal upon starting the X-ray emission and the stop signal for stopping the X-ray emission between the source control unit 15 and the electronic cassette 19. Furthermore, the console 13 receives image data outputted from the electronic cassette 19 and applies various types of image processing such as gamma correction and frequency processing to the image data. The X-ray image after being subjected to the image processing is displayed on the display 29 of the console 13. The data of the X-ray image is stored to the storage device 33 of the console 13, or another data storage device such as an image storage server connected to the console 13 through a network.

The console 13 receives an input of an examination order including information about sex and age of a patient, a body part to be imaged, and an examination purpose, and displays the examination order on the display 29. The examination order is inputted from an external system e.g. HIS (hospital information system) or RIS (radiography information system) that manages patient data and examination data related to radiography, or inputted manually by the operator such as the radiological technician. The operator confirms the contents of the examination order on the display 29, and inputs the imaging condition corresponding to the contents through the input device of the console 13.

Figure 4:
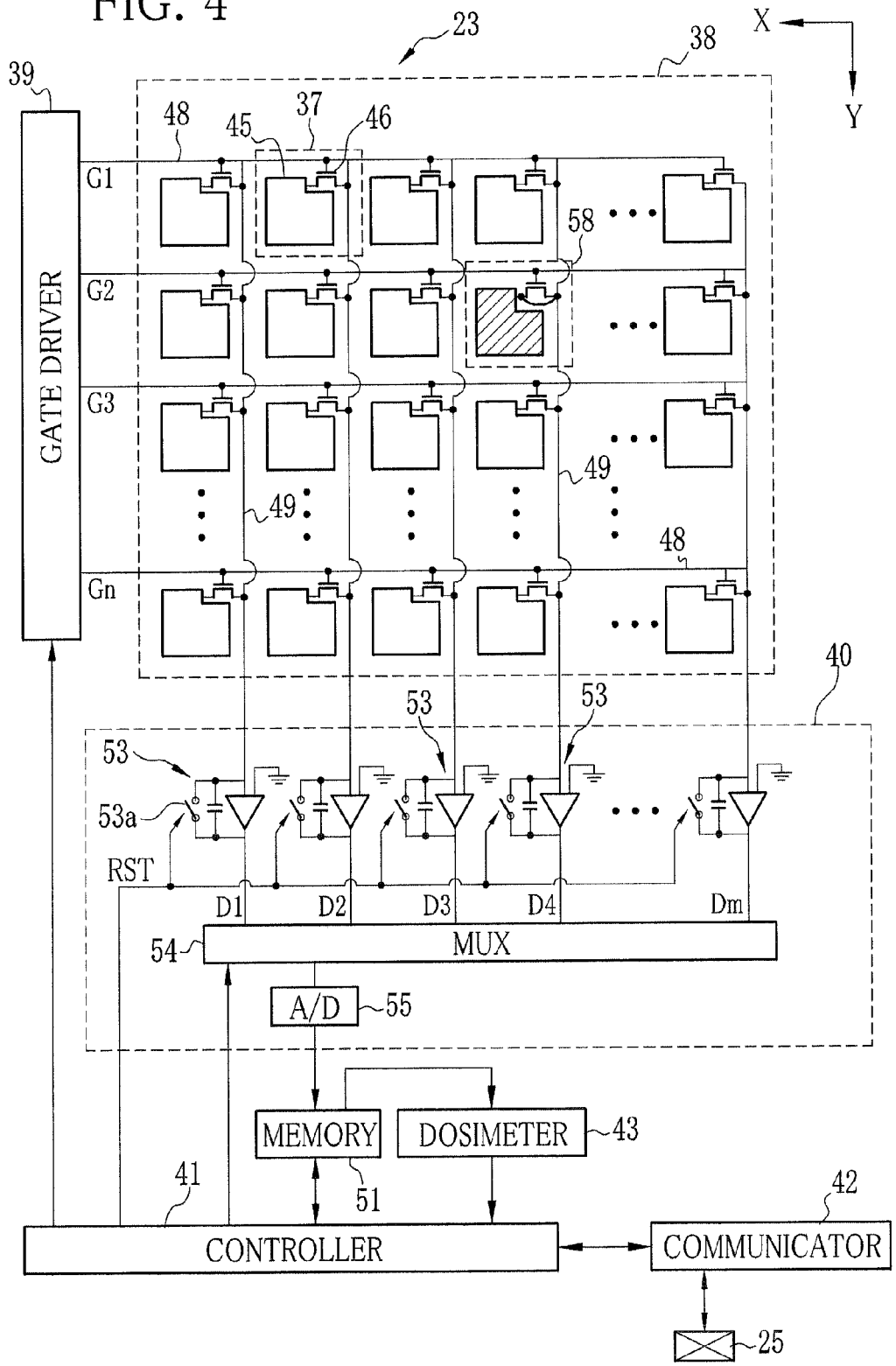
FIG. 4 is an explanatory view showing the electrical structure of the electronic cassette.

In FIG. 4, the FPD 23 has a TFT active matrix substrate. The FPD 23 is provided with a detection panel having an image capturing field 38 in which a plurality of pixels 37 each for accumulating signal charge in accordance with an X-ray amount incident thereon are arranged in the substrate, a gate driver 39 for controlling readout of the signal charge by driving the pixels 37, a signal processing circuit 40 for converting the signal charge read out from the pixels 37 into digital data and outputting the digital data, and a controller 41 for controlling the operation of the FPD 23 by controlling the gate driver 39 and the signal processing circuit 40. The plurality of pixels 37 are arranged into a two-dimensional matrix with n rows (X direction) and m columns (Y direction) at a predetermined pitch. "n" and "m" are integers of two or more. The pixel number of the FPD 23 is, for example, approximately 2000 by 2000.

A communicator 42 that performs communication processing with the communicator 34 of the console 13 through a cable, and a dosimeter 43 that measures an X-ray dose applied to the electronic cassette 19 through the object H are connected to the controller 41. To the communicator 42, the multi-terminal 25 described above is connected. The communicator 42, for example, controls transmission of a signal transmitted or received through the multi-terminal 25 according to a communication protocol. To be more specific, the communicator 42 adds transmission control information (for example, a transmission destination, an IP address of a sender, and the like) determined in the protocol to a transmission signal received from the controller 41, and on the contrary, removes the transmission control information from a reception signal and passes the signal after the removal to the controller 41. In addition, in receiving a signal, the communicator 42 transmits a reception confirmation signal to a sender. The controller 41 corresponds to a first controller or a controller described in the claims, and the communicator 42 corresponds to a first communicator or a communicator of the claims.

The FPD 23 is of an indirect conversion type, having a scintillator (phosphor) for converting the X-rays into visible light. The pixels 37 perform photoelectric conversion of the visible light converted by the scintillator. The scintillator is opposed to the entire image capturing field 38 having an array of the pixels 37. The scintillator is made of CsI (cesium iodide), GOS (gadolinium oxysulfide), or the like. Note that, a direct conversion type FPD, which uses a conversion layer (amorphous selenium or the like) for directly converting the X-rays into the electric charge, may be used instead.

The pixel 37 is composed of a photodiode 45 being a photoelectric conversion element that produces the electric charge (electron and hole pairs) upon entry of the visible light, a capacitor (not shown) for accumulating the electric charge produced by the photodiode 45, and a thin film transistor (TFT) 46 functioning as a switching element.

The photodiode 45 has a semiconducting layer (of a PIN type, for example) of a-Si (amorphous silicon) or the like. An upper electrode and a lower electrode are disposed on the top and bottom of the semiconducting layer, respectively. The lower electrode of the photodiode 45 is connected to the TFT 46. The upper electrode of the photodiode 45 is connected to a bias line (not shown).

Through the bias line, a bias voltage is applied to the upper electrode of the photodiode 45 of every pixel 37 in the image capturing field 38. Since the application of the bias voltage produces an electric field in the semiconducting layer of the photodiode 45, the electric charge (electron and hole pairs) produced in the semiconducting layer by the photoelectric conversion is attracted to the upper and lower electrodes, one of which has a positive polarity and the other of which has a negative polarity. Thereby, the electric charge is accumulated in the capacitor.

A gate electrode of the TFT 46 is connected to a scan line 48. A source electrode of the TFT 46 is connected to a signal line 49. A drain electrode of the TFT 46 is connected to the photodiode 45. The scan lines 48 and the signal lines 49 are routed into a lattice. The number of the scan lines 48 coincides with the number of the rows (n rows) of the pixels 37 in the image capturing field 38. Each scan line 48 is common wiring connected to a plurality of pixels 37 of one row. The number of the signal lines 49 coincides with the number of the columns (m columns) of the pixels 37. Each signal line 49 is common wiring connected to a plurality of pixels 37 of one column. The scan lines 48 are connected to the gate driver 39, and the signal lines 49 are connected to the signal processing circuit 40.

The gate driver 39 drives the TFTs 46 to carry out the accumulation operation for accumulating the signal charge in the pixels 37 in accordance with the amount of the X-rays incident thereon, a readout operation for reading out the signal charge from the pixels 37, and a reset operation for resetting the electric charge accumulated in the pixels 37. The controller 41 controls the start timing of each of the above operations carried out by the gate driver 39.

In the accumulation operation, the signal charge is accumulated in the pixels 37 while the TFTs 46 are turned off. In the readout operation, the gate driver 39 sequentially issues gate pulses G1 to Gn each of which drives the TFTs 46 of the same row at a time. Thereby, the scan lines 48 are activated one by one to turn on the TFTs 46 connected to the activated scan line 48 on a row-by-row basis.

Upon turning on the TFTs 46 of one row, the signal charge accumulated in each of the pixels 37 of one row is inputted to the signal processing circuit 40 through each signal line 49. In the signal processing circuit 40, the signal charge of one row is converted into voltages and outputted. Thus, the output voltages corresponding to the signal charge are read out as voltage signals D1 to Dm. The analog voltage signals D1 to Dm are converted into digital data, and image data that is composed of digital pixel values representing density in each of the pixels of one row is produced. The image data is outputted to a memory 51 contained in the electronic cassette 19.

A dark current occurs in the semiconducting layer of the photodiode 45 irrespective of the presence or absence of entry of the X-rays. Due to the application of the bias voltage, dark charge according to the dark current is accumulated in the capacitor. The dark charge becomes noise of the image data, and therefore the reset operation is carried out to remove the dark charge. The reset operation is an operation to discharge the dark charge occurring in the pixels 37 from the pixels 37 through the signal lines 49.

The reset operation adopts a sequential reset method, for example, by which the pixels 37 are reset on a row-by-row basis. In the sequential reset method, as with the readout operation of the signal charge, the gate driver 39 sequentially issues the gate pulses G1 to Gn to the scan lines 48 to turn on the TFTs 46 of the pixels 37 on a row-by-row basis. While the TFT 46 is turned on, the dark charge is inputted from the pixel 37 through the signal line 49 into the signal processing circuit 40.

In the reset operation, in contrast to the readout operation, the readout of the output voltage in accordance with the dark charge is not carried out. In the reset operation, the controller 41 outputs reset pulses RST to the signal processing circuit 40 in synchronization with the issue of each of the gate pulses G1 to Gn. In the signal processing circuit 40, an input of the reset pulse RST turns on reset switches 53a of integration amplifiers 53 to be described later on, and hence the inputted dark charge is reset.

Instead of the sequential reset method, a parallel reset method or all pixels reset method may be used. In the parallel reset method, a plurality of rows of pixels are grouped together, and sequential reset is carried out in each group, so as to concurrently discharge the dark charge from the rows of the number of the groups. In the all pixels reset method, the gate pulse is inputted to every row to discharge the dark charge from every pixel at a time. The parallel reset method and the all pixels reset method allow speeding up the reset operation.

The signal processing circuit 40 includes the integration amplifiers 53, a MUX 54, an A/D converter 55, and the like. The integration amplifier 53 is connected to each signal line 49 on a one-by-one basis. The integration amplifier 53 is composed of an operational amplifier and a capacitor connected between input and output terminals of the operational amplifier. The signal line 49 is connected to one of the input terminals of the operational amplifier. The other input terminal (not shown) of the operational amplifier is connected to a ground (GND). The integration amplifier 53 converts by integration the signal charge inputted from the signal line 49 into each of the voltage signals D1 to Dm, and outputs the voltage signals D1 to Dm.

The output terminal of the integration amplifier 53 of every column is connected to the MUX 54 through a multiplier (not shown) for multiplying each of the voltage signals D1 to Dm and a sample holder (not shown) for holding each of the voltage signals D1 to Dm. The MUX 54 selects one of the plurality of integration amplifiers 53 connected in parallel, and inputs the voltage signals D1 to Dm outputted from the selected integration amplifiers 53 in series to the A/D converter 55.

The A/D converter 55 converts the inputted analog voltage signals D1 to Dm of one row into digital pixel values in accordance with individual signal levels, and outputs the pixel values to the memory 51. The memory 51 stores the pixel values of one row as image data that represents one row of the X-ray image, with being associated with the coordinates of the individual pixels 37 in the image capturing field 38.

After the voltage signals D1 to Dm of one row are outputted from the integration amplifiers 53, the controller 41 outputs the reset pulse RST to the integration amplifiers 53 to turn on the reset switches 53a of the integration amplifiers 53. Thus, the signal charge of one row accumulated in the integration amplifiers 53 is reset. Upon resetting the integration amplifiers 53, the gate driver 39 outputs the gate pulse of the next row to start reading out the signal charge from the pixels 37 of the next row. By sequential repetition of this operation, the signal charge is read out from the pixels 37 of every row.

After the completion of the readout from every row, the image data representing the X-ray image of one frame is stored in the memory 51. The image data stored in the memory 51 is subjected to image correction processing that includes an offset correction for removing an offset component, being fixed pattern noise caused by individual difference or environment of the FPD 23, and a sensitivity correction for correcting variations in sensitivity of individual photodiodes 45, variations in output properties of the signal processing circuit 40, and the like. The image data is read out from the memory 51, and transmitted to the console 13 through the communicator 42. Thereby, the X-ray image of the object H is detected.

The FPD 23 has the function of detecting the amount of the X-rays applied thereto. As shown in a hatch pattern in FIG. 4, the FPD 23 has short pixels 58 in addition to the pixels 37 in the image capturing field 38. The short pixel 58 functions as a dose detection sensor for detecting the applied amount of the X-rays. The short pixel 58 always shorts out to the signal line 49, while the pixel 37 and the signal line 49 are electrically connected and disconnected by turning on and off the TFT 46.

The structure of the short pixel 58 is similar to that of the pixel 37. The short pixel 58 has the photodiode 45 and the TFT 46, and the photodiode 45 produces the signal charge in accordance with the amount of the X-rays incident thereon. The structural difference between the short pixel 58 and the pixel 37 is that the short pixel 38 has the source and the drain of the TFT 46 that are short out by wiring to lose the switching function of the TFT 46. Thus, the signal charge produced in the photodiode 45 of the short pixel 58 always flows into the signal line 49, and is inputted to the integration amplifier 53. Note that, instead of wiring the source and the drain of the TFT 46 of the short pixel 58, the photodiode 45 of the short pixel 58 may be directly connected to the signal line 49 without providing the TFT 46 itself.

The controller 41 makes the MUX 54 select the integration amplifiers 53 to which the signal charge from the short pixels 58 is inputted, to read out voltage signals (dose detection signals) of the integration amplifiers 53. The dose detection signals from the integration amplifiers 53 are inputted to the A/D converter 55 and converted into digital values. The digital values are outputted to the memory 51. The digital values are stored to the memory 51 with being associated with the coordinate information of each short pixel 58 in the image capturing field 38. The FPD 23 repeats a plurality of number of such dose detecting operations at a predetermine sampling rate during the X-ray emission.

During the X-ray emission, the dosimeter 43 reads out the dose detection signals from the memory 51. The dosimeter 43 integrates the read dose detection signals to measure an accumulative dose of the X-rays that are applied to the FPD 23 through the object H.

Figure 5:
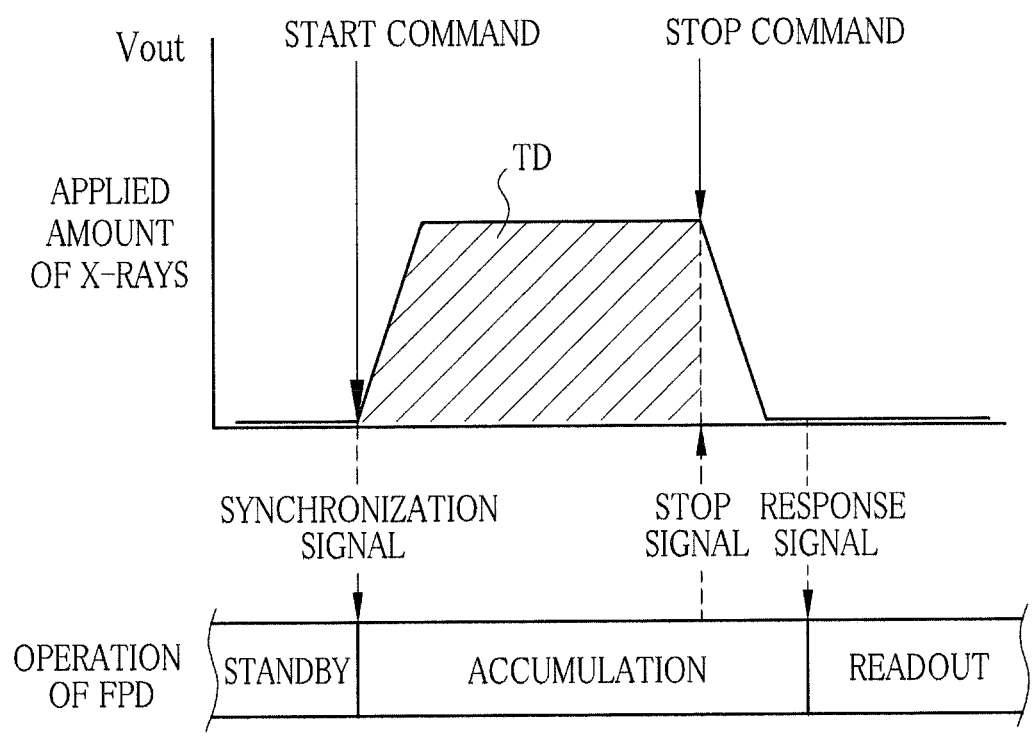
FIG. 5 is an explanatory view showing an X-ray dose and the details of FPD control based on the X-ray dose.

FIG. 5 is a graph that shows an application profile representing variation with time in the amount of the X-rays applied to the FPD 23 per unit of time and the progression of an operational state of the FPD 23 in one imaging operation. In the application profile, the applied amount of the X-rays takes an approximately trapezoidal shape in the graph in which a horizontal axis represents time and a vertical axis represents the applied amount of the X-rays. When the X-ray source 14 starts an X-ray emission upon receiving the start command, the applied amount of the X-rays is gradually increased to a peak value, which is determined in accordance with the tube current set as the imaging condition, and is kept in an approximately steady state in the vicinity of the peak value until receiving the stop command. Then, when the X-ray source 14 stops the X-ray emission upon receiving the stop command, the applied amount of the X-rays is gradually decreases to "0", and the X-ray emission is completely stopped. An area of the application profile represents the accumulative dose.

The controller 41 sets a target dose to be applied based on the imaging condition including the sex and age of the patient, the body part to be imaged, the examination purpose, and the like inputted from the console 13. For example, in FIG. 5, a hatched area is set as a target dose TD. In response to an exposure preparation command inputted from the console 13, the controller 41 shifts the FPD 23 to a standby state. In the standby state, the controller 41 makes the FPD 23 execute the reset operation. As soon as the synchronization signal is inputted from the source control unit 15 at the time of starting an X-ray emission, the controller 41 turns off the TFTs 46 of the pixels 37 and shifts the FPD 23 from the standby state to the accumulation operation. Since the TFTs 46 are turned off, the signal charge is accumulated in the pixels 37 in accordance with the X-ray dose applied thereto.

The short pixels 58 are always short out to the signal lines 49 even though the TFTs 46 of the pixels 37 are turned off, so the dosimeter 43 can measure the accumulative dose of the X-rays applied to the FPD 23 during the X-ray emission based on output of the short pixels 58 flowing into the signal lines 49. The dosimeter 43 integrates the dose detection signal of the short pixel 58 read from the memory 51 to measure the accumulative dose of the X-rays, and inputs the measured accumulative dose to the controller 41. The controller 41 compares the accumulative dose with the target dose. As soon as the accumulative dose of the X-rays has reached the target dose TD, the controller 41 issues the stop signal. The controller 41 inputs the stop signal to the communicator 42, and the communicator 42 transmits the stop signal to the source control unit 15. Note that, the controller 41 functions as a stop signal issuing unit in this embodiment, but the dosimeter 43 may function as the stop signal issuing unit, instead. In this case, the dosimeter 43 compares the measured accumulative dose with the target dose TD, and issues the stop signal as soon as the accumulative dose has reached the target dose TD.

Upon receiving the stop signal, the source control unit 15 transmits the stop signal to the X-ray source 14 to stop the X-ray emission. The controller 41 ends the accumulation operation of the FPD 23 and starts the readout operation, at the instant when the response signal indicating the stop of the X-ray emission is sent back from the source control unit 15. Note that, for the purpose of preventing the occurrence of artifact caused by the X-ray emission during the readout operation of the FPD 23, the response signal is transmitted after the stop of the X-ray emission.

As described above, the electronic cassette 19 and the console 13 are connected through one communication line. Accordingly, if the electronic cassette 19 transmits the stop signal to the source control unit 15 in the course of communicating the control signal between the electronic cassette 19 and the console 13, the transmission of the stop signal may be delayed due to the congestion or collision of communication.

Especially, if the reception timing of the control signal (the life check signal, the state monitoring signal, the calibration command, or the like) by the electronic cassette 19 from the console 13 overlaps the transmission timing of the stop signal from the electronic cassette 19 to the console 13, the congestion or collision of communication tends to occur. Also, the overlap of transmission and reception processing of a plurality of signals applies a heavy load of communication processing on the communicator 42. Furthermore, the electronic cassette 19 has to transmit the response signal to the console 13 in response to the control signal from the console 13. Thus, since the transmission timing of the response signal and the stop signal overlaps, the load of the communication processing on the communicator 42 is increased. For these reasons, the transmission of the stop signal is possibly delayed.

To solve this problem, the controller 41 of the electronic cassette 19 and the CPU 31 of the console 13 regulate the communication between the electronic cassette 19 and the console 13 during the accumulation operation of the FPD 23, until the communicator 42 of the electronic cassette 19 completes the transmission of the stop signal. More specifically, the controller 41 of the electronic cassette 19 makes the communicator 42 perform only the transmission of the stop signal, and stop the transmission and reception of any signal other than the stop signal during the accumulation operation of the FPD 23, until the transmission of the stop signal is completed. The transmission of any signal other than the stop signal includes not only the transmission of the response signal in response to the control signal from the console 13, but also the transmission of the image data that is obtained and recorded in the memory 51 in a previous imaging operation and the like, for example. The communicator 42 stops receiving any signal from the console 13, in addition to stops transmitting any signal other than the stop signal. In other words, the controller 41 of the electronic cassette 19 carries out such communication regulation as to stop every communication, except for the transmission of the stop signal by the communicator 42, during the accumulation operation of the FPD 23 until the transmission of the stop signal is completed.

The CPU 31 of the console 13 regulates the communication with the electronic cassette 19 by controlling the communicator 34. To be more specific, the CPU 31 of the console 13 makes the communicator 34 perform only the mediation of the stop signal transmitted from the electronic cassette 19 and stop the transmission of the control signal (life check signal, the state monitoring signal, the calibration command, or the like) to the electronic cassette 19 during the accumulation operation of the FPD 23.

More specifically speaking, as for the timing of starting the communication regulation, the controller 41 of the electronic cassette 19 and the CPU 31 of the console 13 start the communication regulation of any signal other than the stop signal, upon responding to the synchronization signal that is inputted from the source control unit 15 at the start of an X-ray emission. The communication regulation of any signal other than the stop signal is continued until the transmission of the stop signal is completed, at the least.

Figure 6:
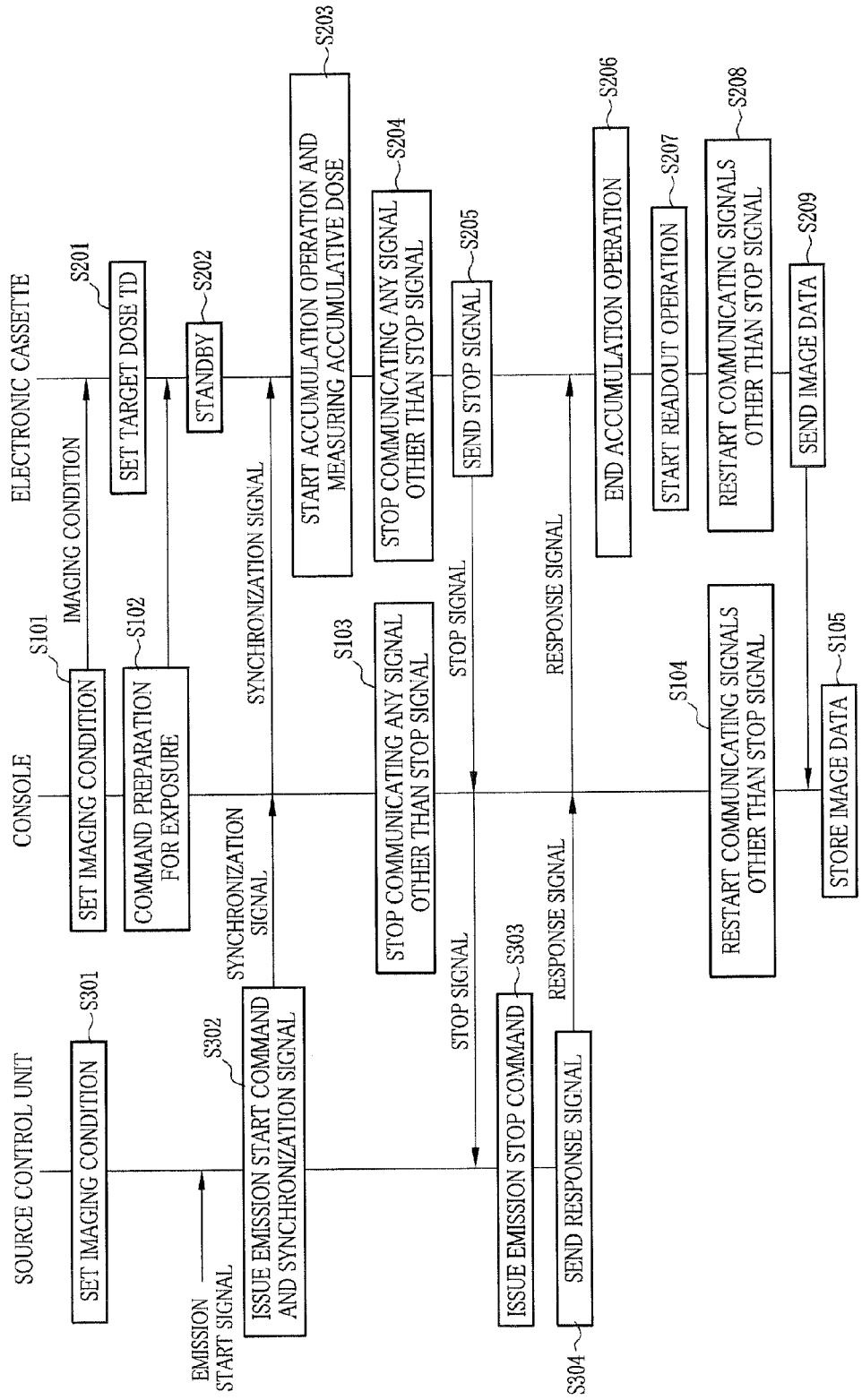
FIG. 6 is a flowchart of imaging processing of the X-ray imaging system.

Referring to a flowchart of FIG. 6, the operation of the X-ray imaging system 10 will be described. The positioning of a body part of an object H and the X-ray source 14 is carried out with respect to the imaging stand 20 loaded with the electronic cassette 19. An examination order including the sex and age of a patient, the body part to be imaged, an examination purpose, and the like is inputted to the console 13, and an imaging condition is set based on the examination order (S101). The console 13 transmits the set imaging condition to the electronic cassette 19 through the communicator 34. The controller 41 of the electronic cassette 19 sets a target dose TD of X-rays based on the imaging condition received by the communicator 42 (S201). To the source control unit 15, the imaging condition including a tube voltage, a tube current, an emission time, and the like is set from the operation panel (S301).

The console 13 issues an exposure preparation command, which makes the electronic cassette 19 prepare for making an exposure, through the communicator 34 to the electronic cassette 19 (S102). In the electronic cassette 19, the FPD 23 is shifted to a standby state, upon receiving the exposure preparation command at the communicator 42 (S202). As soon as an emission start signal is inputted from the emission switch 16, the source control unit 15 inputs an emission start command to the X-ray source 14 (S302). The X-ray source 14 starts applying X-rays to the object H. At the same time, the source control unit 15 transmits a synchronization signal to the electronic cassette 19 through the console 13 (S302). Upon receiving the synchronization signal, the controller 41 of the electronic cassette 19 makes the FPD 23 start an accumulation operation (S203).

The controller 41 integrates an output voltage Vout during the accumulation operation of the FPD 23 to measure an accumulative dose of the X-rays applied to the FPD 23 through the object H (S203). During the accumulation operation of the FPD 23, the console 13 and the electronic cassette 19 make the communicators 34 and 42 stop communicating any signal other than a stop signal, until transmission of the stop signal is completed at the least (S103, S204). The controller 41 compares the accumulative dose of the X-rays with the target dose TD. As soon as the accumulative dose of the X-rays has reached the target dose TD, the controller 41 makes the communicator 42 transmit a stop signal through the console 13 to the source control unit 15 (S205). Upon receiving the stop signal, the source control unit 15 issues a stop command to the X-ray source 14 to stop the X-ray emission (S303).

At the instant when a response signal that indicates the stop of the X-ray emission is sent back from the source control unit 15 (S304), the controller 41 ends the accumulation operation of the FPD (S206), and shifts the FPD 23 to a readout operation (S207). The CPU 31 of the console 13 and the controller 41 of the electronic cassette 19 lift the communication regulation, and make the communicators 34 and 42 restart communicating signals other than the stop signal (S104, S208). Read X-ray image data is transmitted from the electronic cassette 19 to the console 13 (S209), and stored to the storage device 33 (S105) after being subjected to predetermined image processing.

As described above, since the communication of any signal other than the stop signal is stopped during the accumulation operation of the FPD 23, the stop signal is prevented from being delayed by communication congestion or signal collision. Thus, it is possible to stop the X-ray emission from the X-ray source 14 at appropriate timing, and minimize unnecessary radiation exposure of the object H. Also, stopping the X-ray emission at appropriate timing prevents application of an excessive dose beyond the target dose TD, and allows obtainment of the X-ray image of preferable image quality.

As for the communication regulation during the accumulation operation of the FPD 23, the above embodiment describes a case in which every communication between the electronic cassette 19 and the console 13 is stopped except for the communication of the stop signal, but an error notification that is transmitted from the electronic cassette 19 to the console 13 may be excluded from the signals under the communication regulation. This is because the error notification, which notifies the operator of the occurrence of an error, requires rapidity in most cases.

In the above embodiment, both of the controller 41 of the electronic cassette 19 and the CPU 31 of the console 13 control the communicators 42 and 34, respectively, to carry out the communication regulation. However, the communication regulation between the communicators 42 and 34 may be carried out under the control of at least one of the controller 41 and the CPU 31.

For example, only the CPU 31 of the console 13 may carry out such control over the communicator 34 as to stop transmission processing of the control signal (life check signal, the state monitoring signal, and the like) to the electronic cassette 19. In other words, the controller 41 of the electronic cassette 19 may carry out no control related to the communication regulation over the communicator 42.

This is because main signals to be transmitted from the electronic cassette 19 to the console 13 are the response signal responding to the control signal from the console 13, the error notification, and the image data. Out of these signals, in the case of transmitting the error notification, it is conceivable that the electronic cassette 19 often fails to function normally and make an appropriate exposure, irrespective of the presence or absence of a delay in the stop signal. Also, it is conceivable that the image data transmitted during the accumulation operation of the FPD 23 is not the image data of a current exposure (under accumulation) but the image data of a previous exposure, as described above. The image data of the previous exposure should have been completely transmitted before starting the current accumulation operation in most cases, so transmission processing is hardly carried out during the accumulation operation of the FPD 23. Thus, there is not much need for the electronic cassette 19 to actively stop the transmission of the error notification and the image data.

On the other hand, the response signal that responds to the control signal periodically transmitted from the console is produced more often than the error notification and the image data do, and hence there is much need to stop the transmission of the response signal. However, the transmission of the response signal is triggered by the control signal from the console 13, so transmission processing of the response signal does not happen in the electronic cassette 19 unless the control signal is transmitted to the electronic cassette 19. Accordingly, stopping the transmission of the control signal in the console results in stopping the transmission processing of the electronic cassette 19, even if the electronic cassette 19 does not stop the transmission processing actively.

For the above reasons, the communication regulation by the CPU 31 of the console 13 for stopping the transmission processing of the control signal (life check signal, the state monitoring signal, and the like) to the electronic cassette 19 can bring about the effect of the present invention, that is, the prevention of a delay in the stop signal.

It is conceivable as a matter of course that there is a signal, such as the image data of the previous exposure, transmitted from the electronic cassette 19 to the console 13 during the accumulation operation of the FPD 23, though it hardly happens, as described above. Thus, stopping the communication of any signal other than the stop signal in the electronic cassette 19 ensures the effect of the present invention, that is, the prevention of a delay in the stop signal.

Note that, only the electronic cassette 19 may carry out the communication regulation, instead of the console 13. For example, the controller 41 of the electronic cassette 19 may carry out such control as to stop reception processing of the control signal, by making the communicator 42 abandon the control signal from the console 13. This can eliminate a load of response processing to the control signal on the controller 41 and the communicator 42. However, the console 13 to which no communication regulation is applied continues transmitting the control signal, so this case has a little effect on reduction of the communication congestion or collision in a transmission line. Also, there can be a case that the console 13 judges it abnormal to receive no response to the control signal from the electronic cassette 19. Therefore, the regulation control is preferably carried out by both of the console 13 and the electronic cassette 19 as described above or by only the console 13.

In the above embodiments, the life check signal, the state monitoring signal, the calibration command, the error notification, and the image data are described as the signals to be subjected to the communication regulation during the accumulation operation of the FPD 23, but an arbitrary signal may be subjected to the communication regulation as long as the signal affects a delay in the stop signal.

In the above embodiments, the X-ray dose is detected by the short pixels provided in the image capturing field. The short pixel has approximately the same structure and X-ray sensitivity as the normal pixel has, and hence can detect the X-ray dose with high accuracy. The same structure also allows ease of manufacture and low cost increase.

Figure 7:
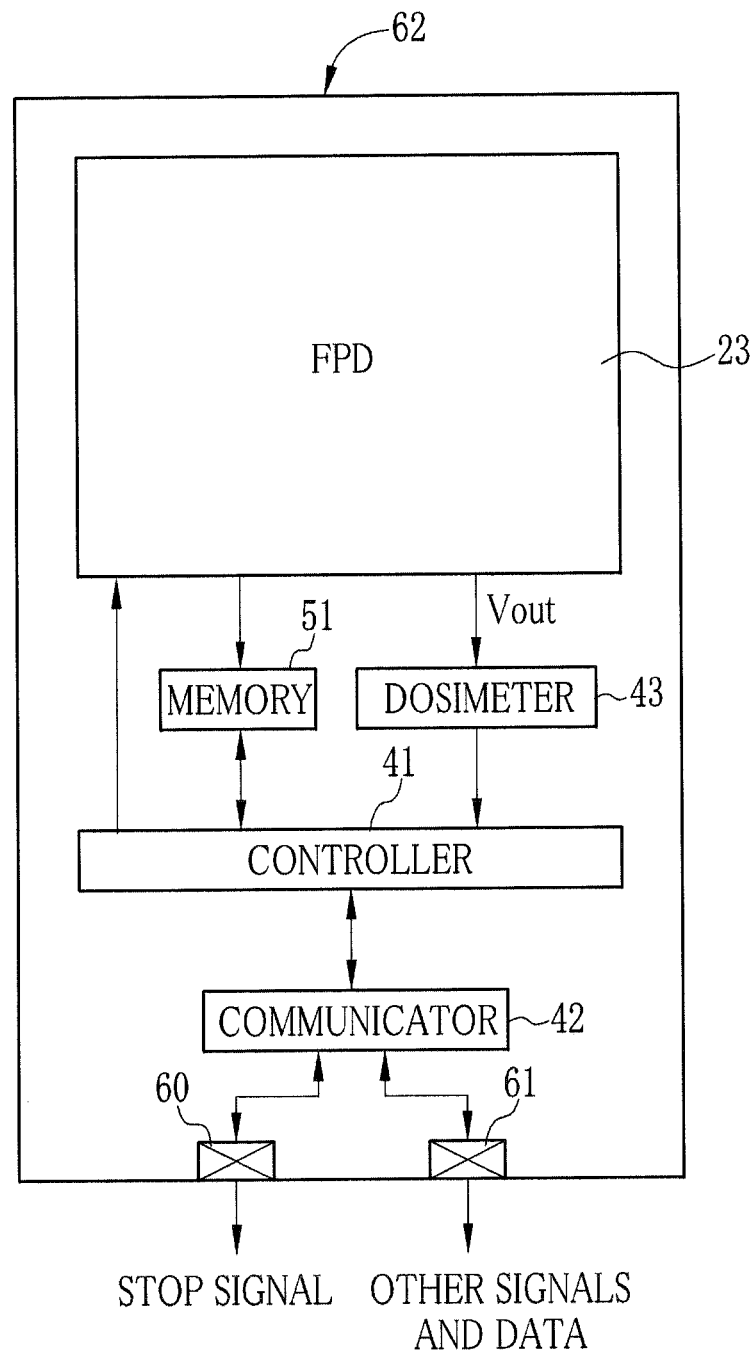
FIG. 7 is a block diagram showing the electrical structure of an electronic cassette having a plurality of communication ports.

In the above embodiments, the electronic cassette 19 is provided with only one multi-terminal 25 being the communication port. However, the present invention is applicable to another electronic cassette 62, as shown in FIG. 7, in which a plurality of communication ports 60 and 61 are connected to the communicator 42. One communication port 60 is dedicated to the transmission of the stop signal and the other port 61 is dedicated to the transmission of the other signals and data, for example. Providing the plurality of communication ports reduces communication congestion and signal collision in each communication port. However, increase in the number of signals transmitted and received by the communicator 42 put a heavy load of processing to be applied to the signals transmitted and received through each port on the communicator 42, and may cause a communication delay. An X-ray emission time is several tens of microseconds in some cases, depending on a body part to be imaged. In the case of rapidly transmitting the stop signal in such a short time, a slight increase in a load on the communicator 42 may heavily affect a communication delay. However, according to the present invention, regulating communication of any signal other than the stop signal during the accumulation operation of the FPD 23 can reduce a redundant load on the communicator 42 and concentrate the processing ability of the communicator 42 at processing of the stop signal. Therefore, it is possible to prevent a communication delay in the stop signal.

In addition to providing the plurality of communication ports, a plurality of communicators 42 that are in charge of communication processing, e.g. a first communicator dedicated to the stop signal and a second communicator being in charge of communication processing of the signals other than the stop signal, may be provided. According to this method, since the first communicator performs only the communication processing of the stop signal, a load on the first communicator is reduced. Also, the communication ports are isolated from signal to signal, a communication delay owing to communication congestion and signal collision is reduced. Therefore, it is possible to prevent a communication delay in the stop signal.

Even in the case of providing the plurality of communicators, however, the present invention is effectively applied to certainly prevent a communication delay in the stop signal. This is because providing the plurality of communicators requires the controller 41 to perform centralized control of the plurality of communicators, and brings about increase in a load on the controller 41. In other words, in a case where the plurality of communicators perform the communication processing at the same time, the load on the controller 41 is increased because of increase in the number of devices placed under the centralized control. If a delay occurs in the centralized control of the controller 41, the communication processing of each of the plurality of communicators is delayed too. Accordingly, even in the case of providing the plurality of communicators, the communication of any signal other than the stop signal is preferably regulated during the accumulation operation of the FPD.

Furthermore, providing the plurality of communicators has the demerits of increasing costs for providing the ports and space for disposing the communicators. To eliminate such demerits, one communicator is preferably provided. Also, since the electronic cassette has the small housing, it is difficult to obtain space for the communicators therein. Providing one communicator is especially effective in the electronic cassette.

In the above embodiments, the communicator 42 independent of the controller 41 performs the communication processing, but all or a part of the functions of the communicator 42 may be integrated into the controller 41.

Furthermore, the present invention is not limited to the above embodiments, and can take various configurations within the confines of claims of the present invention, as a matter of course.

In the above embodiments, the cable-type communicators connect among the console 13, the source control unit 15, and the electronic cassette 19. The present invention, however, is applicable to an X-ray imaging system having wireless-type communicators, or an X-ray imaging system having both the cable-type and wireless-type communicators.

The X-ray dose may be detected by a method other than the short pixels. For example, a detection pixel having a TFT for dose detection, in addition to a TFT for image reading as with the TFT of the normal pixel, may be provided and used as the dose detection sensor. In the detection pixel, the TFT for dose detection is turned on in detecting the dose to output the dose detection signal, while the TFT for image reading is turned on in reading the image to output the image signal.

A part of the pixels are not necessarily used as the dose detection sensor, such as the short pixel and the detection pixel. The dose detection sensor may be provided between adjoining pixels, for example. Otherwise, for example, the photodiode composing the pixel is applied with the bias voltage, and a bias current flowing through the bias line varies in accordance with the amount of the signal charge produced in the photodiode. By detecting the bias current, the X-ray dose may be detected. In the case of detecting the bias current, the dose detection sensor is composed of the bias line and a measurement unit for measuring the bias current. Otherwise, even in a state of turning off the TFT of the pixel, a slight leak current flows through the signal line in accordance with the amount of the signal charge produced in the photodiode. By detecting the leak current, the X-ray dose may be detected. In the case of detecting the leak current, the dose detection sensor is composed of the signal line and a measurement unit for measuring the leak current.

The TFT type FPD in which the TFT matrix substrate is made of the glass substrate is described as an example, but the FPD may have a CMOS image sensor or a CCD image sensor using a semiconductor substrate. Using the CMOS image sensor has the following merit. The CMOS image sensor can perform a so-called nondestructive read by which signal charge accumulated in each pixel is read out as a voltage signal through an amplifier provided in the pixel without flowing out to a signal line for readout. According to this, it is possible to detect the X-ray dose even in the accumulation operation by selecting an arbitrary pixel in the image capturing field and reading out the signal charge from the pixel. Therefore, in the case of using the CMOS image sensor, it is possible to share any of the normal pixels as the dose detection sensor, without using a specific dose detection sensor as with the short pixel described above.

In the above embodiments, at that point in time when the response signal is sent back from the source control unit 15 in response to the transmission of the stop signal, the accumulation operation is ended, and the communication regulation is lifted to restart the communication of the signals other than the stop signal. However, at the instant when the short pixels 58 detect the actual stop of the X-ray emission after transmitting the stop signal, instead of the response signal, the accumulation operation may be ended and the communication regulation may be lifted. As a method for detecting the actual stop of the X-ray emission, there is a method using the short pixels 58, as an example. The dose detection operation is continued using the short pixels 58 even after transmitting the stop signal, and the dosimeter 43 detects the actual stop of the X-ray emission based on the dose detection signal. Since the stop of the X-ray emission makes a signal value of the dose detection signal to substantially zero, monitoring the signal value of the dose detection signal makes it possible to detect the actual stop of the X-ray emission.

In the above embodiments, after the completion of the accumulation operation, the communication regulation is lifted and the communication of the signals other than the stop signal is restarted. However, after the completion of the accumulation operation and then after the readout operation for reading out image information has been completed, the communication regulation may be lifted and the communication of the signals other than the stop signal may be restarted. This is because an analog voltage signal outputted from the FPD 23 is susceptible to noise until being subjected to an A/D conversion, so the restart of the communication after the completion of the readout operation is more preferable in terms of preventing degradation in image quality.

Note that, in a case where the communication regulation is lifted after the completion of the readout operation, the timing of restarting the communication of the signals other than the stop signal is delayed by time of the readout operation, as compared with the case of lifting the communication regulation immediately after the completion of the accumulation operation as described in the above embodiments, but this affects little in view of an entire imaging operation. Accordingly, the timing of lifting the communication regulation is preferably set after the completion of the readout operation, to give a high priority to preventing the occurrence of noise in the readout operation. Also, the transmission of the stop signal during the accumulation operation of the FPD 23 causes deterioration in the image quality more or less, but stopping at least the transmission of the other signals can minimize deterioration in the image quality.

In the above embodiments, the stop signal is transmitted from the electronic cassette to the X-ray generating apparatus through the console, but may be transmitted from the electronic cassette to the X-ray generating apparatus directly without through the console. Also in this case, stopping the transmission of the signals from the console to the electronic cassette during the accumulation operation of the FPD until completing the transmission of the stop signal allows the electronic cassette to concentrate the capacity of the communicator on the transmission of the stop signal, and hence has the effect of preventing the communication delay of the stop signal. Note that, in this case, the electronic cassette notifies the console of the start of the accumulation operation and the transmission of the stop signal at that point in time when they occur. The notifications allow the console to grasp a current operational state of the electronic cassette.

In the above embodiments, the communication between the electronic cassette and the console is regulated, as an example. However, if the electronic cassette communicates with a device other than the console, the electronic cassette may regulate that communication.

In the above embodiments, the electronic cassette 19 into which an entire control circuit is integrated is described as an example, but the present invention is applicable to an X-ray image detecting device that has an electronic cassette with an FPD and an external control unit connected wiredly or wirelessly to the electronic cassette, for example. In this case, the communication regulation may be performed between the console and the control unit and between the control unit and the electronic cassette. The console may be composed of a main unit having an image display function and an image processing function and a control unit having the function of controlling the electronic cassette. In this case, the communication regulation may be performed between the control unit and the electronic cassette. Furthermore, the present invention may be applied to a stationary X-ray image detecting device, instead of the electronic cassette being a portable X-ray image detecting device.

The present invention is applicable to an imaging system using another type of radiation such as γ-rays, instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging system comprising:
   (A) a radiation image detecting device including:
   an image detector having an image capturing field having an array of a plurality of pixels for accumulating an electric signal in accordance with an incident amount of radiation from a radiation generating apparatus, for detecting a radiographic image;
   a dosimeter for measuring a dose of said radiation emitted from said radiation generating apparatus and passed through an object;
   a stop signal issuing unit for issuing a stop signal to make said radiation generating apparatus stop an emission of said radiation in accordance with said dose of said radiation measured by said dosimeter;
   a first communicator for performing communication processing of said stop signal for transmitting said stop signal to said radiation generating apparatus during an accumulation operation of said image detector, and performing communication processing of a signal other than said stop signal; and
   a first controller for controlling said first communicator, and
   (B) a console for controlling said radiation image detecting device, said console including:
   a second communicator for performing communication processing of a control signal for transmitting said control signal to said first communicator; and
   a second controller for controlling said second communicator, wherein
   during said accumulation operation, communication regulation for regulating communication of a signal other than said stop signal between said first communicator and said second communicator is performed by controlling at least one of said first controller and said second controller, at least until said first communicator completes transmission of said stop signal.

2. The radiation imaging system according to claim 1, wherein said signal to which said communication regulation is applied includes said control signal.

3. The radiation imaging system according to claim 2, wherein said control signal includes at least one of a life check signal for checking an actuation state of said radiation image detecting device, a state monitoring signal for checking a state including a temperature of said radiation image detecting device, and a calibration command for commanding said radiation image detecting device to execute a calibration.

4. The radiation imaging system according to claim 1, wherein said stop signal is transmitted to said radiation generating apparatus through said console.

5. The radiation imaging system according to claim 1, wherein said communication regulation includes processing in which at least one of said first communicator and said second communicator stops all or a part of communication of said signals other than said stop signal.

6. The radiation imaging system according to claim 5, wherein said second controller of said console stops transmitting said control signal from said second communicator to said first communicator to carry out said communication regulation.

7. The radiation imaging system according to claim 5, wherein said first controller of said radiation image detecting device stops communication of said signal other than said stop signal from said first communicator to carry out said communication regulation.

8. The radiation imaging system according to claim 1, wherein said communication regulation carried out by at least one of said first controller and said second controller is lifted after said first communicator completes transmission of said stop signal.

9. The radiation imaging system according to claim 8, wherein said communication regulation is lifted after receiving a response signal for indicating a stop of said emission of said radiation from said radiation source.

10. The radiation imaging system according to claim 8, wherein said communication regulation is lifted after completing said accumulation operation and furthermore completing a readout operation for reading out said radiographic image from said image detector.

11. The radiation imaging system according to claim 8, wherein said communication regulation is lifted after said dosimeter has detected an actual stop of said emission of said radiation.

12. The radiation imaging system according to claim 1, wherein said radiation image detecting device has one said first communicator that is shared between communication of said stop signal and communication of said signal other than said stop signal.

13. The radiation imaging system according to claim 12, wherein only one communication port is connected to said first communicator, and said communication port is shared between communication of said stop signal and communication of said signal other than said stop signal.

14. The radiation imaging system according to claim 12, wherein a plurality of communication ports are connected to said first communicator, and one of said communication ports is dedicated to transmission of said stop signal.

15. The radiation imaging system according to claim 1, wherein in said radiation image detecting device, a dose detection sensor is provided in said image capturing field of said image detector to output a dose detection signal to said dosimeter.

16. The radiation imaging system according to claim 15, wherein said dose detection sensor uses a part of said pixels.

17. The radiation imaging system according to claim 1, wherein said radiation image detecting device is an electronic cassette having said image detector contained in a portable housing.

18. The radiation imaging system according to claim 1, wherein said stop signal issuing unit issues said stop signal, upon said dose of said radiation measured by said dosimeter reaching a target dose.

19. A control method of a radiation imaging system having a radiation image detecting device and a console for controlling said radiation image detecting device, said control method comprising the steps of:
   accumulating an electric signal in a plurality of pixels arranged in an image capturing field in accordance with an incident amount of radiation from a radiation generating apparatus to detect a radiographic image in said radiation image detecting device;

measuring a dose of said radiation emitted from said radiation generating apparatus and passed through an object in said radiation image detecting device;

issuing a stop signal to be transmitted to said radiation generating apparatus to make said radiation generating apparatus stop an emission of said radiation in accordance with said measured dose, in said radiation image detecting device; and regulating communication of a signal other than said stop signal between said radiation image detecting device and said console in said accumulation step, at least until said radiation image detecting device completes transmission of said stop signal.

20. A radiation image detecting device comprising:

an image detector having an image capturing field having an array of a plurality of pixels for accumulating an electric signal in accordance with an incident amount of radiation from a radiation generating apparatus, for detecting a radiographic image;

a dosimeter for measuring a dose of said radiation emitted from said radiation generating apparatus and passed through an object;

a stop signal issuing unit for issuing a stop signal to make said radiation generating apparatus stop an emission of said radiation in accordance with said dose of said radiation measured by said dosimeter;

a communicator for performing communication processing of said stop signal for transmitting said stop signal to said radiation generating apparatus during an accumulation operation of said image detector, and performing communication processing of a signal other than said stop signal; and a controller for regulating communication of said signal other than said stop signal by said communicator during said accumulation operation, at least until said communicator completes transmission of said stop signal.

21. The radiation image detecting device according to claim 20, wherein said communication regulation includes processing in which said communicator stops all or a part of communication of said signals other than said stop signal.

22. The radiation image detecting device according to claim 21, wherein said controller stops communication of said signal other than said stop signal by said communicator to carry out said communication regulation.

23. The radiation image detecting device according to claim 20, wherein said communication regulation carried out by said controller is lifted after said communicator completes transmission of said stop signal.

24. The radiation image detecting device according to claim 23, wherein said communication regulation is lifted after receiving a response signal for indicating a stop of said emission of said radiation from said radiation source.

25. The radiation image detecting device according to claim 23, wherein said communication regulation is lifted after completing said accumulation operation and furthermore completing a readout operation for reading out said radiographic image from said image detector.

26. The radiation image detecting device according to claim 23, wherein said communication regulation is lifted after said dosimeter has detected an actual stop of said emission of said radiation.

27. The radiation image detecting device according to claim 20, wherein there is one said communicator that is shared between communication of said stop signal and communication of said signal other than said stop signal.

28. The radiation image detecting device according to claim 27, wherein only one communication port is connected to said communicator, and said communication port is shared between communication of said stop signal and communication of said signal other than said stop signal.

29. The radiation image detecting device according to claim 27, wherein a plurality of communication ports are connected to said communicator, and one of said communication ports is dedicated to transmission of said stop signal.

* * * * *